United States Patent
Sainz Prestel et al.

(10) Patent No.: US 8,877,262 B2
(45) Date of Patent: Nov. 4, 2014

(54) VEGETABLE EXTRACT AND METHOD OF USE AS AN ACTIVE PRINCIPLE IN THE PRODUCTION OF A PHARMACOLOGICALLY ACTIVE PRODUCT FOR THE TREATMENT OF TISSUE LESIONS, AND METHOD FOR OBTAINING THE EXTRACT

(71) Applicant: Valeria Lucila Sainz Prestel, Las Rozas de Madrid (ES)

(72) Inventors: Valeria Lucila Sainz Prestel, Las Rozas de Madrid (ES); Adrian Alonso Sainz Gutierrez, Santa Cruz de la Sierra (BO)

(73) Assignee: Valeria Lucila Sainz Prestel, Las Rozas de Madrid (ES)

( * ) Notice: Subject to any disclaimer, the term of this patent is extended or adjusted under 35 U.S.C. 154(b) by 0 days.

(21) Appl. No.: 14/247,666

(22) Filed: Apr. 8, 2014

(65) Prior Publication Data

US 2014/0205690 A1     Jul. 24, 2014

Related U.S. Application Data

(62) Division of application No. 14/000,017, filed as application No. PCT/ES2012/000032 on Feb. 16, 2012, now Pat. No. 8,715,750.

(30) Foreign Application Priority Data

Feb. 16, 2011    (ES) .................................. 201100167

(51) Int. Cl.
     *A01N 65/00*      (2009.01)
     *A61K 36/60*      (2006.01)
     *B29C 45/00*      (2006.01)

(52) U.S. Cl.
     CPC ................. *A61K 36/60* (2013.01); *B29C 45/00* (2013.01)
     USPC ....................................................... 424/725

(58) Field of Classification Search
None
See application file for complete search history.

(56) References Cited

U.S. PATENT DOCUMENTS

| | | |
|---|---|---|
| 5,464,439 A | 11/1995 | Gendler |
| 6,258,778 B1 | 7/2001 | Rodgers et al. |

FOREIGN PATENT DOCUMENTS

| | | |
|---|---|---|
| ES | 2334298 | 3/2010 |
| WO | 0002905 | 1/2000 |
| WO | 2005115090 | 12/2005 |
| WO | 2009141835 | 11/2009 |

OTHER PUBLICATIONS

Abdulla et al. Biomedical Research 2010, vol. 21, No. 3, p. 241-245, "Role of *Ficus deltoidea* extract in the enhancement of wound healing in experimental rats."

Coelho-Ferreira., Journal of Ethnopharmacology 2009, vol. 126, p. 159-175 "Medicinal knowledge and plant utilization in an Amazonian coastal community of Maruda, Para State, Brazil."

De Feo et al. Journal of Ethnopharmacology 1992 vol. 36, p. 113-125, "Traditional phytotherapy in the Peninsula Sorrentina, Campania, Southern Italy."

Roy et al. International Journal of PharmTech Research Jul.-Sep. 2009, vol. 1, No. 3, p. 506-508, "Wound Healing Potential of Leaf Extracts of *Ficus religiosa* on Wistar albino strain rats."

Lansky et al. Journal of Ethnopharmacology 2008, vol. 119, p. 195-213, "*Ficus* spp., fig: Ethnobotany and potential as anticancer and anti-inflammatory agents."

Sanz-Biset et al. Journal of Ethnopharmacology 2009, vol. 122, p. 333-362, "A first survey on the medicinal plants of the Chazuta valley, Peruvian Amazon."

Tene et al. Journal of Ethnopharmacology 2007, vol. 111, p. 63-81, "An ethnobotanical survery of medicinal plants used in Loja and Zamora-Chinchipe, Ecuador."

Mahyar et al. Journal of Ethnopharmacology 1991, vol. 31, p. 217-237, "Medicinal Plants of Seberida, Riau Province, Sumatra, Indonesia."

Zamora-Martinez et al. Journal of Ethnopharmacology 1992 vol. 35, p. 229-257. "Medicinal plants used in some rural populations of Oaxaza, Pueble and Verazruz, Mexico."

International Search Report for PCT/ES2012/000032, English translation attached to original, Both completed by the Spanish Patent Office on May 29, 2012, All together 9 Pages.

Park et al. Korean Journal Physiol Pharmacol. Dec. 2009, vol. 13, p. 417-424, "Hexane-Soluble Fraction of the Common Fig, *Ficus carica*, inhibits Osteoclast Differentiation in Murine Bone Marrow-Derived Macrophages and RAW 264.7 Cells."

*Primary Examiner* — Michael Meller
(74) *Attorney, Agent, or Firm* — Brooks Kushman P.C.

(57) ABSTRACT

A method for treatment of acute and/or chronic tissue lesions disorder is disclosed. A resin extract from *Ficus pertusa* L. f and/or *Ficus eximia* Schott is administered to a patient in need thereof as an active principle for producing a pharmacologically active product for the treatment of acute and/or chronic tissue lesions, both of bone tissue and of soft tissue.

6 Claims, No Drawings

VEGETABLE EXTRACT AND METHOD OF USE AS AN ACTIVE PRINCIPLE IN THE PRODUCTION OF A PHARMACOLOGICALLY ACTIVE PRODUCT FOR THE TREATMENT OF TISSUE LESIONS, AND METHOD FOR OBTAINING THE EXTRACT

CROSS-REFERENCE TO RELATED APPLICATION

This application is a divisional of U.S. Ser. No. 14/000,017 filed Aug. 16, 2013, which is the U.S. national phase of PCT Application No. PCT/ES2012/000032 filed on Feb. 16, 2012, which claims priority to Spanish Patent Application No. P201100167 filed on Feb. 16, 2011, the disclosures of which are incorporated in their entirety by reference herein.

FIELD OF TECHNOLOGY

The invention relates to the area of medicine, more concretely to the treatment of infectious and traumatic processes and of tissue lesions in general.

PRIOR ART

At present, in the area of the treatment of tissue lesions, various methods and substances are being investigated and applied with the aim of achieving tissue regeneration, advances that are constantly evolving and on which considerable effort is being expended given the complex nature of the regeneration of tissues, especially those involved in infectious processes.

In cases of treatment of processes that involve bone tissue, materials and methods are applied which, whether or not combined, promote three basic mechanisms: osteogenesis, osteoconduction and osteoinduction (U.S. Pat. No. 5,464,439). Common methods in the mechanisms of osteogenesis are those that promote osteoconduction using autologous bone graft, which supplies live osteocomponent cells, alone or combined with plasma rich in growth factors or with bone morphogenetic proteins (osteoinductive mechanism), and although this method presents complications relating to lysis of the graft or infection thereof, it is currently the one most recommended. Regarding osteoinduction, which refers to the process of stimulation of osteogenesis, promoting the release of inductive proteins that facilitate cellular differentiation, substances are used such as plasma rich in growth factors, which is obtained from the patient's own blood, recombinant human bone morphogenetic proteins, especially rhBMP-2 and rhBMP-7 and bone growth factors, such as rhGDF-5 among others (patent document WO0002905).

Regarding processes that involve soft tissues, various methods are known and applied that promote tissue regeneration by methods such as grafts and tissue transplants, cultures of stem cells and so-called tissue engineering (Spanish patent application P200702694). The methods described in the prior art have difficulties in their application for tissue regeneration when acute and/or chronic infectious processes are involved, so that it is seen to be necessary and advisable to develop novel methods and products allowing effective treatment of said disorders.

The use of plant species for the treatment of diseases and lesions has been widely documented since ancient times, so that currently, according to the World Health Organization, about 25% of the global medical pharmacopeia is based on medicinal products derived directly from plants and apparently this might, directly or indirectly, be extended over the years. However, no mention is found in the medical literature of the use of products based on vegetable extracts that have demonstrated activity in the cleaning and healing of lesions that involve destruction of bone tissue. The same can be said of the treatment of soft tissue lesions, especially cases of synergistic necrotizing cellulitis or of pressure ulcers, which cause extensive areas of tissue necrosis accompanied by infections that are difficult to nip in the bud.

In odontology there are combinations of extracts of various plants that include, among their components, an extract of the genus *Ficus* in the prevention and/or treatment of periodontal processes, however, there is no reference to its use in isolated form (as single extract), neither for the treatment of periapical processes nor of furcal lesions or in infections after tooth extraction, specifically in alveolitis, nor in cases of osteomyelitis of the jaw.

The use of resin in toto from various species of *Ficus* in natural medicine is not new, since its properties as anthelmintic are known in various regions of the world. Moreover, analgesic, anti-inflammatory, rubefacient, and antirheumatic properties have been described for medicinal products that use the plant species alone or in combination with other varieties.

Furthermore, among other compounds derived from *Ficus*, there is ficin, which is a proteolytic enzyme whose activity is widely known, being commonly employed industrially as a meat tenderizer and in the clarification of beer.

Compositions have been described based on extracts of some varieties of *Ficus*, specifically of *Ficus benghalensis, Ficus religiosa, Ficus infectoria* and *Ficus racemosa*, in synergistic combination with antimicrobial properties and for wound healing (document WO2005115090). The synergistic combination of the extract of said plant species is described as effective against a wide range of bacteria such as *Staphylococcus aureus, Lutea sareina, Streptococcus pyogenes, Streptococcus pneumoniae*, vancomycin-resistant enterococci, *E. coli, Ps. aeruginosa, S. typhi*, of *E. coli* (MDR), *Acinetobacter, Proteus mirabilis* etc.

Patent document WO2005115090 also describes a method for treating and healing burns including chemical, electrical and radiation burns, as well as lesions caused by contusions, by topical application of a combination of extracts of *Ficus religiosa, Ficus infectoria* and *Azadirachta indica* mixed with one or more pharmaceutically acceptable vehicles.

However, to date there has not been any description of the use of extracts of *Ficus pertusa* L. f nor of *Ficus eximia* Schott, species endemic to Central America and South America, applied in the treatment of acute infectious lesions that cause extensive soft tissue necrosis, such as occurs in cases of synergistic necrotizing cellulitis, gangrene, pressure ulcers or in cases of enterocutaneous fistulas. Owing to the limited distribution of both species, since *Ficus pertusa* only occurs in the tropical rainforests that extend from the south of Mexico to Paraguay and *Ficus eximia* in the tropical rainforests of Bolivia, Brazil, Paraguay, Peru, Venezuela and Costa Rica, there are hardly any descriptions of industrial uses or of the therapeutic properties of said species.

Technical Problem to be Solved

The increased morbidity and high mortality rates, in certain disorders associated with chronic and acute tissue lesions, make it desirable to obtain a pharmacologically active product for treating lesions of this type and which allows the problem to be solved effectively, simply and safely.

The present invention is based on the use of a natural extract, as an essential component of a product, whose activity promotes tissue regeneration in acute and chronic infectious processes, allowing them to be treated simply, effectively and without adverse effects.

DETAILED DESCRIPTION OF THE INVENTION

1. The present invention relates to the use of the resin extract of the tree *Ficus pertusa* L.f and/or *Ficus eximia* Schott as active principle for producing a pharmacologically active product for the treatment of acute and/or chronic tissue lesions, both of bone tissue and of soft tissue, in particular for cleaning and healing osteomyelitic lesions that involve destruction of bone tissue; promoting osteointegration of implants; consolidation of fractures in general and in cases of pseudoarthrosis; preventing infectious processes of bone tissue; cleaning and healing of soft tissues, especially in cases of synergistic necrotizing cellulitis, pressure ulcers, diabetic foot ulcer and/or processes with extensive areas of tissue necrosis accompanied by acute infectious processes; treatment of periapical odontological processes; furcal lesions; osteomyelitis of the jaw; alveolitis; periodontitis; as promoter of osteointegration of dental implants and prevention of infectious processes thereof.

The invention also relates to obtaining an extract of *Ficus pertusa* and/or *Ficus eximia*, as active principle for producing a pharmacologically active product for the treatment of acute and/or chronic tissue lesions, both of bone tissue and of soft tissue.

An advantageous method for obtaining the resin on which the extraction according to the invention will be performed is carried out on trees, preferably adult, of the family Moraceae of the genus *Ficus*, and can be carried out either on the species *Ficus pertusa* or on *Ficus eximia*, preferably applying the following method:

Oblique cuts are made in the bark, making the lower apex of each cut coincide with a vertical channel made in the trunk of the tree. At the bottom of the channel, a container preferably of glass is positioned for receiving the exudation that emerges from the cuts made in the bark of the tree.

Once the resin has been obtained, it is put in a hermetically sealed container and is stored preferably at a temperature between 1° C. and 4° C.

An advantageous method for obtaining the extract consists of carrying out two extractions, firstly, a liquid-liquid extraction using a solvent of medium polarity such as ethyl acetate for example, and then carrying out solid-liquid methanolic extraction. The method can be carried out advantageously in the following manner:

Making a liquid-liquid extract by mixing the resin with a solvent of medium polarity, it being possible to use, as a nonlimiting example, ethyl acetate in a proportion ideally of 10 times the volume of the solvent of medium polarity relative to the volume of the resin. This mixture is stirred at a temperature between 30° C. and 45° C., for a period ideally of 24 hours. Once the liquid of the first extraction has been separated, the method is repeated at least twice more, achieving, by sedimentation, separation of the extracts obtained and the solid residues, obtaining on the one hand a liquid extract and a gray-colored solid residue.

The solid residue resulting from separation of the extract with ethyl acetate is mixed with a polar solvent, it being possible to use, as a nonlimiting example, methanol, ethanol, butanol or other polar solvents, in a proportion ideally of 2 times the volume of the polar solvent relative to the volume of the residue. This mixture is stirred at a temperature between 30° C. and 45° C. for a period of 24 hours, subsequently achieving, by sedimentation, separation of the undesirable solutes, obtaining, once the solvent has been removed, a liquid extract of a dark brown color. Once dried, this extract constitutes the water-soluble solid extract that constitutes the active principle for producing a pharmacologically active product for the treatment of acute and/or chronic tissue lesions, both of bone tissue and of soft tissue.

Regardless of the manner of preparation used according to the invention, subsequent steps can be added that aim to favor storage and/or stabilization without thereby altering the actual nature of the extract.

The water-soluble extract obtained according to the description can be used as a single compound or in combination with pharmacologically acceptable vehicles for topical use thereof.

The invention will be better understood and its advantages will be clearer from the following nonlimiting examples, given solely for purposes of illustration.

Examples Illustrating Application of the Invention for Odontological Lesions

In February 2001, a clinical trial protocol was initiated, intended for odontological patients with chronic and acute periapical processes, conducting 78 treatments on 68 subjects with various disorders such as chronic periapical processes, infectious abscessed pulpitis, pulpal necrosis, pulp gangrene, then extended to cases of periodontitis and alveolitis. The amount of extract deposited in the canal at each application was 150 mg and the number of applications varied from one to ten during the treatment.

Case 1.—Woman of 17 years, who had a vestibular abscess in tooth 4/6, with grade II mobility. Radiologically, deep resinous filling, with furcal and distal periapical lesion. Root canal treatment was begun on Feb. 19, 2001 with 150 mg of resin extract of *Ficus pertusa*, which was deposited using a lentulo in the root canal in its third proximal to the pulp chamber. Progress was favorable and 11 days after the first application, with the tooth fixed and asymptomatic, check-up radiography showed furcal and periapical cortical regeneration. After five applications the tooth was filled definitively on Mar. 16, 2001. At the last check-up nine-and-a-half years later, she remained clinically asymptomatic and radiologically lesion-free.

Case 2.—Man of 52 years, with a jacket with porcelain crown on tooth 4/5 and history of previous apicectomy with retrograde treatment. On Oct. 16, 2007, he had acute pain, and radiography showed a chronic periapical process. As it was impossible to withdraw the intraroot pin, a small hole was made directly above the periapical process, through which a small fragment of collagen sponge soaked in 200 mg of resin extract of the genus *Ficus*, species Eximia Schott, diluted in 1 cc of sterile distilled water, was introduced. It was not combined with systemic medication. At a check-up after 48 hours, the subject reported being asymptomatic and having been pain-free since the procedure described was performed. Being asymptomatic, radiography a month later showed disappearance of the radiolucent area.

Case 3.—Woman of 35 years, after extraction of tooth 2/4 presented alveolitis sicca, having received as treatment multiple periosteotomies of the cavity, combined with antibiotics and anti-inflammatories, the latter giving rise to drug-induced gastritis. On Dec. 20, 2004, as the subject had acute pain, the resin extract of the genus *Ficus* was administered as 50%/50% mixture of the species *Ficus pertusa* and *Ficus eximia*. The treatment consisted of depositing a fragment of collagen sponge soaked in 200 mg of extract diluted in 1 cc of sterile distilled water in the alveolar cavity and primary closure of the gum. Starting from this moment the subject had relief of symptoms. Radiography eighteen months after the treatment showed bone regeneration with conservation of the space, without bone retraction.

Examples Illustrating Application of the Invention, Other Types of Bone Lesions

The extract can also be applied in cases of osteomyelitis of bones of any type, and for this, in patients who have a well-formed fistula, it is possible to inject, with a fine probe of type K-33 which is led through the external orifice, 200 mg diluted in 5 cc of sterile distilled water, every six days while the orifice is kept viable, and varying the possible number of applications from two to ten. In other cases, if there is an open cavity with the bone tissue exposed, topical treatments can be carried out, using collagen sponges or gauzes soaked in a sterile solution that includes the extract, in sufficient amount (3 g/l).

Case 1.—Woman of 82 years, with diagnosis of tuberculous osteomyelitis of the shaft of the right radius, had had external fistulous orifice with purulent secretion at the anterior face of the right forearm for two years. At the time of examination she reported pain in the right upper limb, which required daily analgesic medication. On Jun. 25, 2004, treatment was initiated by injecting 300 mg of resin extract of *Ficus pertusa*, diluted in 5 cc of sterile distilled water, through a fine probe led through the path of the fistula. Weekly applications of the extract were scheduled, following the same procedure. After the second application, the subject could discontinue the analgesic medication. After the third application, being asymptomatic, and the purulent secretion having disappeared and with radiological evidence of the start of bone regeneration, specific treatment for tuberculosis was begun. The extract was applied during nine sessions, and it was necessary to force introduction of the probe in the last three owing to the process of healing of the external fistulous orifice. As a result, the bone tissue was restored ad integrum, as was verified in check-up X-rays taken at 12 and 18 months after starting the treatment, as well as in computerized axial tomography carried out at three-and-a-half years. The subject remained asymptomatic since the second week after the start of medication with the extract and maintained her usual lifestyle starting from the first application.

Case 2.—Man of 50 years, diagnosed with osteomyelitis of the left ascending branch of the lower jaw, with involvement of the parotid gland, with purulent secretion via left lateral submandibular orifice, trigeminal neuralgia, increase in volume of the left side of the face and trismus. He reported having had a dental implant four months previously, which was removed after a month because of infection, having undergone, two months later, drainage of a subcutaneous abscess, by left submandibular incision. On Apr. 14, 2007, treatment was initiated with 300 mg of resin extract of *Ficus eximia*, diluted in 5 cc of sterile distilled water, applied through a fine probe led through the fistula. Six days later, the subject reported less pain, there was improved opening of the oral cavity, decreased volume of the left side of the face and there was no longer suppuration through the orifice, which was occluded, so that it was necessary to force introduction of the probe in order to apply the second and last dose of the same extract. After this application, the patient returned to his usual work. Progress was favorable despite the degree of bone necrosis that he had in the left branch of the jaw, which moreover included a fracture of the condyle, as was verified clinically and by check-ups with computerized axial tomography. Fourteen months after the treatment, a check-up by computerized axial tomography showed restoration ad integrum of the jaw. A normal mechanism of mastication was verified clinically, moreover with normal secretion of saliva from the left parotid.

Case 3.—Man of 31 years of age, with a history of fracture of the left corner of the lower jaw due to a facial injury, which required, in the period of time between Feb. 2, 2007 and May 17, 2007, five surgical interventions for reduction, osteosynthesis and bone graft from the iliac crest, accompanied by cleanings and sequestrectomies through the implanted osteomyelitis from the postoperative of the first. He had fetid suppuration via left submaxillary fistula, increase in volume of the masseteric region, pain and limited mouth opening. On Nov. 26, 2007, computerized axial tomography was performed, which revealed, at the level of the bone graft, lysis of the spongiosa, pseudoarthrosis thereof with both borders of the body of the mandible, where two miniplates are located, which are not osteointegrated. Treatment was initiated with 300 mg of 50%/50% mixture of resin extract of *Ficus pertusa* and *Ficus eximia*, diluted in 5 cc of sterile distilled water, applied through a fine probe led through the path of the fistula, repeating the applications of the same extract once weekly for a month. At the end of the fourth session, there was evident decrease in volume of the left masseteric region, increased opening of the mouth, little serous secretion and disappearance of the pain. A check-up by computerized axial tomography two years and four months from the start of the treatment revealed osteointegration of the screws and miniplate and integration of the graft at the borders of the jaw forming a single piece; moreover, conservation in width and height of the space left after extraction of tooth 3/7, carried out in the course of the treatment, was observed.

Examples Illustrating Application of the Invention in Lesions of Soft Tissues

Subjects with acute infectious pathology that caused necrosis of subcutaneous cellular tissue, specifically synergistic necrotizing cellulitis, pressure ulcers; diabetic foot lesions; gangrene of the toes; enterocutaneous fistulas of the colon and wounds with loss of substance, were treated with the extract according to the invention.

Case 1.—Woman of 29 years with a septic picture, due to synergistic necrotizing cellulitis that comprises perineum, left gluteus, posterior and anterior face of left thigh, left labium majus of the vulva and inferior quadrants of the anterior wall of the abdomen. Surgical cleaning was carried out, removing the necrotic tissue, leaving extensive areas without skin, which were covered with gauze soaked in 3 grams of the extracts combined in proportions of 50/50% of the resins of *Ficus pertusa* and *Ficus eximia*, diluted in one liter of isotonic saline solution. In addition, discharge colostomy was performed and bladder catheterization, plus water/electrolyte support and antibiotic therapy. Treatments were carried out every three days, withdrawing a very small extra amount of necrotic tissue, always leaving the gauzes soaked in solution that contains the aforementioned combined extract in a proportion of 3 g per liter of isotonic saline solution. Progress was favorable, making it possible, after two weeks, to close some of the areas from which skin had been removed, such as abdominal wall, and both thighs, leaving the left gluteus for closure by second intention.

Case 2.—Diabetic man of 68 years, with a diagnosis of synergistic necrotizing cellulitis in the left thigh including an extensive area without skin and aponeurosis, which comprised from the upper third of the leg on its anterior face, ascended via the patellar region and covered the two lower thirds of the external face of the thigh, with necrotic skin margins and covered with necrosed, foul-smelling tissue. The subject had a history of amputation of the right lower limb at the thigh, owing to synergistic necrotizing cellulitis in previous years. On Aug. 22, 2009, treatment was initiated, which did not involve any debridement, simply covering the whole area with gauzes soaked in 3 g of resin extract of *Ficus pertusa* diluted in one liter of isotonic saline solution. After two days there was evident improvement of the infection, continuing in the manner described for four more applications. On completion of the treatment, the tissues were left clean, covered with granulation tissue, and it was recommended to continue with skin grafts.

Case 3.—Man of 35 years, with history of epilepsy and paraplegia. He had sepsis due to a deep, infected pressure ulcer, which included the whole sacrolumbar region, extending to both buttocks. On Jun. 14, 2008, in addition to the general measures, topical treatment was initiated, applying collagen sponges soaked in 3 grams of resin extract of *Ficus eximia*, diluted in one liter of isotonic saline solution, without any surgical debridement, which was repeated 8 times, every 4 days. At the end of the first application, cleaning of the lesion and the presence of granulation tissue were observed. After the eighth application the subject was referred for reconstructive surgery.

Conclusions

Investigation of the activity of the extract according to the invention together with evaluation of the cases studied in the preclinical and clinical protocols showed that it has the following properties:

1.—It has a potent analgesic and anti-inflammatory effect: The results obtained in preclinical tests, on male Swiss mice weighing 20-25 grams showed that the extract according to the invention possesses activity capable of blocking responses of the inflammatory type in animals, with a potent analgesic effect in models of pain of the inflammatory type. This was corroborated in the clinical tests, since most of the patients were pain-free after the first applications, which made it possible to avoid the use of additional analgesic or anti-inflammatory medication in said protocols.

2.—It has an antimicrobial effect: Cultures and antibiograms were carried out on the material obtained from root canals, demonstrating in vitro good sensitivity to Gram-positive bacteria, especially *Streptococcus pneumoniae*. This property explains the resolution of the infectious process in the cases in which antibiotic therapy was not used. The cases of alveolitis resolved rapidly after the treatment. In the cases of osteomyelitis of the jaw and long bones, in which according to the cultures, several types of bacteria were present, including Koch's bacillus, the results were always favorable, even the case of osteomyelitis of the tibia which kept an exposed canal open, which did not receive adjuvant antibiotic therapy, despite which the foul-smelling suppuration that it presented disappeared completely at the end of the second application of the extract according to the invention. Moreover, in the cases of soft tissue necrosis, the cleaning and asepsis achieved with the extract in a short time is evidence of its antimicrobial efficacy.

3.—It stimulates tissue regeneration: In the clinical studies conducted on dental disorders, in 100% of cases the action of the extract promoted very regular bone growth, completely covering the bone defect or cavity, regenerating not only spongy but also cortical tissue and periodontal ligament. It was also shown that in short periods of approximately a week, the pharmacological action of the extract promoted the fixation of teeth (cases with grade II mobility changed in one week to grade I mobility and in two weeks, complete fixation), even in teeth that suffered root resorption. In radiological follow-ups, carried out on lesions of the jaw and long bones treated with the extract according to the invention, uniform repair of the cavities lacking bone network was also found. In the exposed areas of soft tissue, after the first treatment, the pharmacological action of the extract according to the invention for stimulating angiogenesis was observed, granulation tissue quickly forming, and subsequently covering the defect.

4.—It crosses the inflammatory and infectious barrier: In the clinical studies conducted on dental disorders, through radiological monitoring of osteogenic filling of the cavity it was observed that after the treatment with the extract according to the invention there were no longer any radiolucent gaps or niches that potentially could trigger new infections. Moreover, the clinical studies conducted on osteomyelitis in general demonstrated, through radiological check-ups, harmonious growth of bone tissue. In cases of soft tissue necrosis, it was found that the extract according to the invention provides proteolytic cleaning action, rapidly cleaning all areas of the lesion.

5.—It is bioabsorbable: In the protocols of clinical tests, this property of the extract was verified, since no traces of the medication were found in the subsequent root canal treatments, applications, check-ups and examinations.

6.—Capacity for diffusion: In clinical studies conducted on dental disorders, it was observed that the extract according to the invention diffuses through the root canal and dentinal tubules. Accordingly, in those cases when, owing to the characteristics of the canals or because of previous treatments, it was not possible to reach the root apex, application of the invention in a median, distal segment or even in the pulp chamber did not interfere with resolution of the disorder. This could be determined not only in clinical follow-up but also in X-ray plates, in which it was verified that the obturation did not reach the apex, and also explains the success achieved in resolution of the infection and osteolysis of the cases of furcal lesion. In cases where for various reasons it was not possible to gain access to the canal, the extract's capacity for diffusion meant that the treatments could be carried out by application of the extract through a small hole made directly on the periapical defect, from where it then diffuses to the root canal and to the dentinal tubules, as is corroborated by the resolution of the pathological picture.

7.—It quickly limits acute infectious lesions: In clinical studies conducted on dental disorders, it was observed that in cases of acute infection, the pharmacological effect of the extract according to the invention promoted almost immediate limitation of the bone lesions.

8.—Stability: In the course of the research it was verified that the extracts maintained their activity without any decrease in efficacy after five years of storage at room temperature and without any type of additive or hermetic isolation.

The invention claimed is:

1. A method of treating an acute or chronic tissue lesion selected from the group consisting of synergistic necrotizing cellulitis, pressure ulcers, diabetic foot ulcer, and combinations thereof in a patient in need thereof comprising administering a resin extract of *Ficus pertusa* L. f. and *Ficus eximia*

Schott to said patient, wherein the administering includes 150-300 mg of a 50:50 mixture of *Ficus pertusa* and *Ficus eximia*, diluted in 1-5 milliliters of sterile distilled water, applied through a fine probe led through a path of a fistula to the patient in need thereof, and repeating applications of the 150-300 mg of a 50:50 mixture of *Ficus pertusa* and *Ficus eximia*, diluted in 1-5 milliliters of sterile distilled water, once weekly for a month until the lesions are treated.

2. The method of claim 1, further comprising cleaning and healing osteomyelitic lesions that involve destruction of bone tissue in said patient.

3. The method of claim 1, further comprising promoting osteointegration of implants in said patient.

4. The method of claim 1, further comprising promoting and accelerating consolidation of bone fractures in said patient.

5. The method of claim 1, further comprising consolidation of bone callus in cases of pseudoarthrosis in said patient.

6. The method of claim 1, further comprising treating infectious processes of bone tissue in said patient.

* * * * *